United States Patent [19]
Little et al.

[11] Patent Number: 5,119,408
[45] Date of Patent: Jun. 2, 1992

[54] ROTATE/ROTATE METHOD AND APPARATUS FOR COMPUTED TOMOGRAPHY X-RAY INSPECTION OF LARGE OBJECTS

[75] Inventors: Francis H. Little, Cincinnati; Andrew J. Galish, West Chester; Ralph G. Isaacs, Cincinnati, all of Ohio

[73] Assignee: General Electric Company, Cincinnati, Ohio

[21] Appl. No.: 607,337

[22] Filed: Oct. 31, 1990

[51] Int. Cl.⁵ .............................................. G01N 23/02
[52] U.S. Cl. ........................................ 378/4; 378/10; 378/20; 378/58
[58] Field of Search .................... 378/4, 10, 20, 57, 58, 378/62, 208

[56] References Cited
U.S. PATENT DOCUMENTS

| | | | |
|---|---|---|---|
| 3,766,387 | 10/1973 | Heffan et al. | 250/83.3 |
| 4,422,177 | 12/1983 | Mastronardi et al. | 378/17 |
| 4,600,998 | 7/1986 | Huet | 364/507 |
| 4,989,225 | 1/1991 | Gupta et al. | 378/10 |

Primary Examiner—Janice A. Howell
Assistant Examiner—David P. Porta
Attorney, Agent, or Firm—Charles L. Moore, Jr.; Jerome C. Squillaro

[57] ABSTRACT

A method for inspecting a component having dimensions larger than a fan beam angle of an x-ray inspection system includes the steps of: providing an x-ray beam having a selected fan angle in a source focal point; positioning a portion of the component substantially completely within the x-ray beam; rotating the component 360 degrees around a component inspection rotational axis; collecting the attenuated x-ray beam that passes through the component during rotation; generating a multiplicity of electrical signals responsive to the collected x-ray beam; incrementally moving the component inspection rotational axis about the x-ray source focal point to position another portion of the component within the x-ray beam; and repeating the steps of rotating the part 360 degrees about a component inspection rotational axis and incrementally moving the part inspection rotational axis about the x-ray source focal point until the entire component has passed through the fan beam.

17 Claims, 4 Drawing Sheets

ROTATE/ROTATE METHOD AND APPARATUS FOR COMPUTED TOMOGRAPHY X-RAY INSPECTION OF LARGE OBJECTS

BACKGROUND OF THE INVENTION

The present invention relates to x-ray inspection using Computed Tomography (CT) and, more particularly, to a novel method and apparatus for inspecting large objects such as a gas turbine engine component, rocket engine component, or the like, using a rotate/rotate CT x-ray inspection system.

CT systems are known, and include a source of radiation and an associated detector both of which can be moved, relative to an object under inspection for purposes of reconstructing a cross-sectional area or slice through the object at a selected location on the object by means of penetrating the object with radiation and detecting the attenuation of the radiation caused by the object on an opposite side of the object from the radiation source. The resolution and quality of the image of the cross-sectional slice of the object is dependent upon the precision with which the relative positions of the radiation source, detector and object remain constant during examination of the object. Therefore, most CT systems, such as those used in medicine, have the radiation source, detector and object fixed in position relative to one another while the attenuated radiation signals are detected to reconstruct the cross-sectional slice of the object. Maintaining the relative positions of the radiation source, detector and object is not possible, however, when the object under test is so large that it cannot completely fit within the field of view or fan angle of an x-ray source/detector system.

Presently known x-ray inspection systems for large objects, such as those systems disclosed in U.S. Pat. Nos. 4,422,177; 4,600,998; and 3,766,387, typically inspect the component or part by a rotate/translate method to obtain complete data for reconstruction of an image of a selected cross-sectional area of the component. Referring to FIG. 1, the rotate/translate method involves positioning the component at an initial angle of orientation relative to an x-ray beam 12 and then translating the component 10 linearly through the x-ray beam 12 along a line of travel, indicated by broken line 14 in FIG. 1, substantially perpendicular to a centerline 16 between the focal point 18 of the x-ray source 20 and the center of a detector 22. Attenuated x-ray beam data is collected by the detector as the component is translated or passed linearly through the beam 12. The component is then incrementally rotated about a component inspection rotational axis 22 to a new angular orientation relative to x-ray beam 12; then the component is translated again through x-ray beam 12 while data is collected on the attenuation of the beam by detector 20. This process is repeated until sufficient data is accumulated to construct an image of the cross-sectional slice through the component.

Typically, before each translation through the x-ray beam, the component is rotated through an angle alpha about the same as the fan angle of the x-ray system, or less, to provide sufficient data to reconstruct the cross-sectional image. This process can require that the component be incrementally rotated and translated several times to obtain sufficient angular data to generate an image of sufficient resolution and quality. If the component is rotated by about the x-ray beam fan angle before each translation through the x-ray beam, the minimum number of passes through the x-ray beam required to obtain sufficient data to reconstruct a cross-sectional image will be equivalent to the sum of the fan angle plus 180° divided by the fan angle and rounded to the next highest integer. For example, if the fan angle is about 20°, then at least 10 passes through the x-ray beam would be required to reconstruct the cross-sectional image.

Thus, the rotate/translate method can require considerable mechanical manipulation to acquire sufficient data to reconstruct a cross-sectional image with good resolution. Data acquisition can therefore be quite time consuming, depending upon the size of the part, the fan angle and the angle by which the part is incrementally rotated before each pass through the x-ray beam. In high volume production processes, such as gas turbine engine manufacturing or the like, inspection of very large components by the rotate/translate method can be very inefficient.

Another disadvantage of using the rotate/translate method for inspection of large objects is that the component geometry does not remain at a constant distance from the x-ray focal point as the component is translated linearly through the x-ray beam. This requires additional computer software and computational time to adjust the data to compensate for the change in component geometry before the cross-sectional image is reconstructed.

SUMMARY OF THE INVENTION

It is, accordingly, a primary object of the present invention to provide a novel method and apparatus for examining a large object using x-ray Computed Tomography which is not subject to the foregoing disadvantages.

It is another object of the present invention to provide a CT method and apparatus which is efficient and easily integrated into a high volume production environment.

It is a further object of the present invention to provide a novel method and apparatus for inspecting a component which requires only a single pass through the x-ray beam.

In accordance with the invention, a method for inspecting a component having a dimension larger than a fan beam angle of an x-ray inspection system includes the steps of: (a) providing an x-ray beam having a selected fan angle and a source focal point; (b) positioning a portion of the component substantially completely within the x-ray beam; (c) rotating the component 360 degrees about a component inspection rotational axis; (d) collecting the attenuated x-ray beam that passes through the component during rotation; (e) generating a multiplicity of electrical signals responsive to the collected attenuated x-ray beam; (f) incrementally moving the component inspection rotational axis around the x-ray source focal point to position a next portion of the component within the x-ray beam, the component inspection rotational axis remaining at a selected radius from the x-ray source focal point after movement of the inspection rotational axis; (g) repeating steps (c), (d), (e) and (f) until all portions of the component to be inspected have passed through the x-ray fan beam; and (h) combining the electrical signals in step (e) to construct a cross-sectional image of the component at a selected location. The component may be moved laterally along the component inspection rotational axis to permit reconstruction of a cross-sectional image of the component at another selected location, or the x-ray source focal point and x-ray collecting means may be moved parallel with the component inspection rotational axis to permit reconstruction of a cross-sectional image of the component at another location perpendicular to the inspection rotational axis In accordance with the invention, an apparatus for inspecting a large component includes an x-ray source for generating a beam having a focal point, and first means for rotating the component 360 degrees around a component inspection rotational axis with at least a portion of the components within the x-ray beam. Second means are provided for incrementally rotating the component around the x-ray source focal point to position a next portion of the component within the x-ray beam. The component inspection rotational axis is maintained at a selected radius from the x-ray source focal point after each incremental rotation. Detector. means are provided for collecting the attenuated x-ray beam that passes through the component when the component is rotated 360 degrees around the component inspection rotational axis.

These and other objects of the invention, together with the features and advantages thereof, will become apparent from the following detailed specification when read with the accompanying drawings in which like reference numerals refer to like elements.

DETAILED DESCRIPTION OF THE PREFERRED EMBODIMENTS

Figure 2:
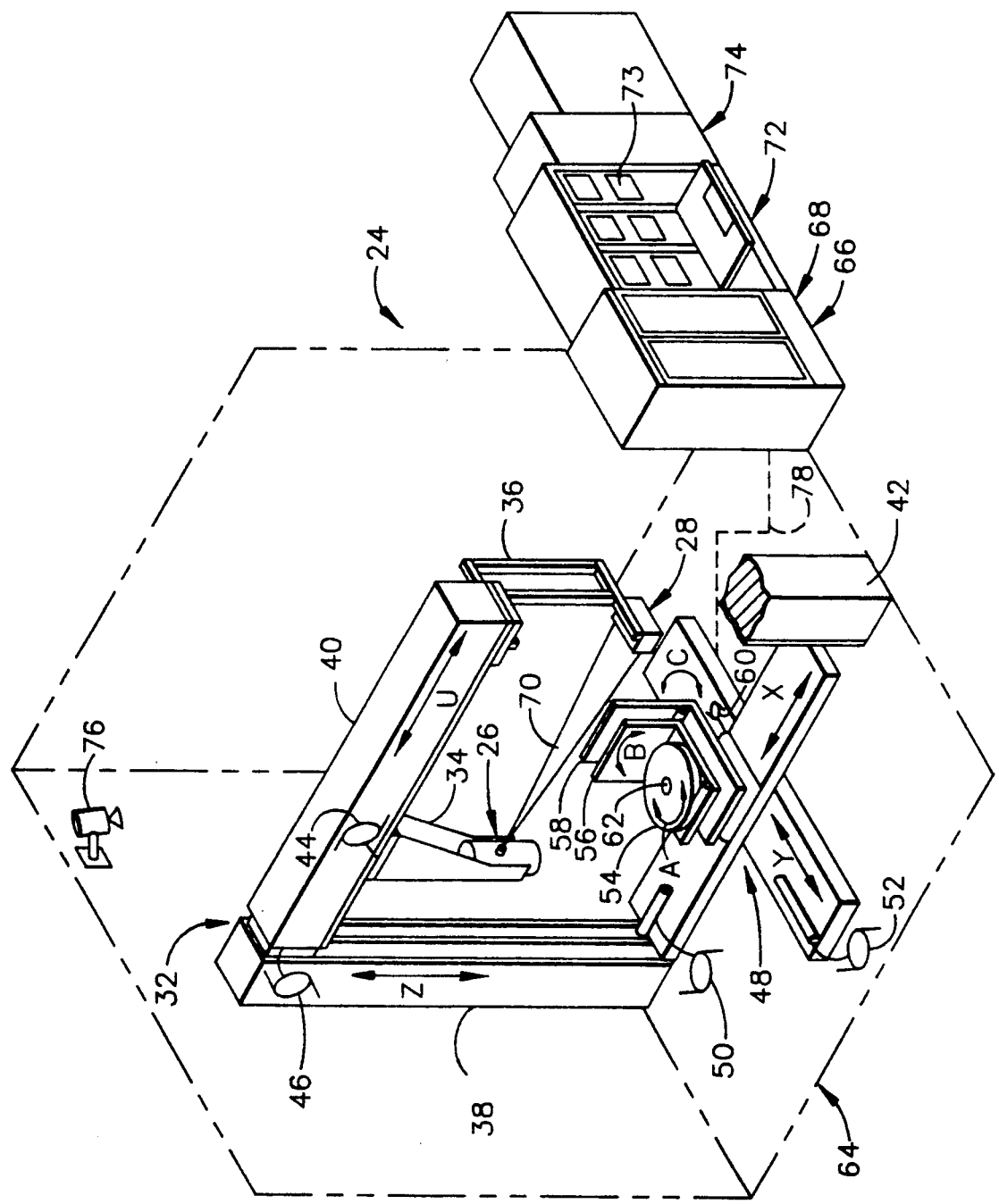
FIG. 2 is a perspective view of a rotate/rotate CT x-ray inspection system in accordance with the invention.
Figure 3A:
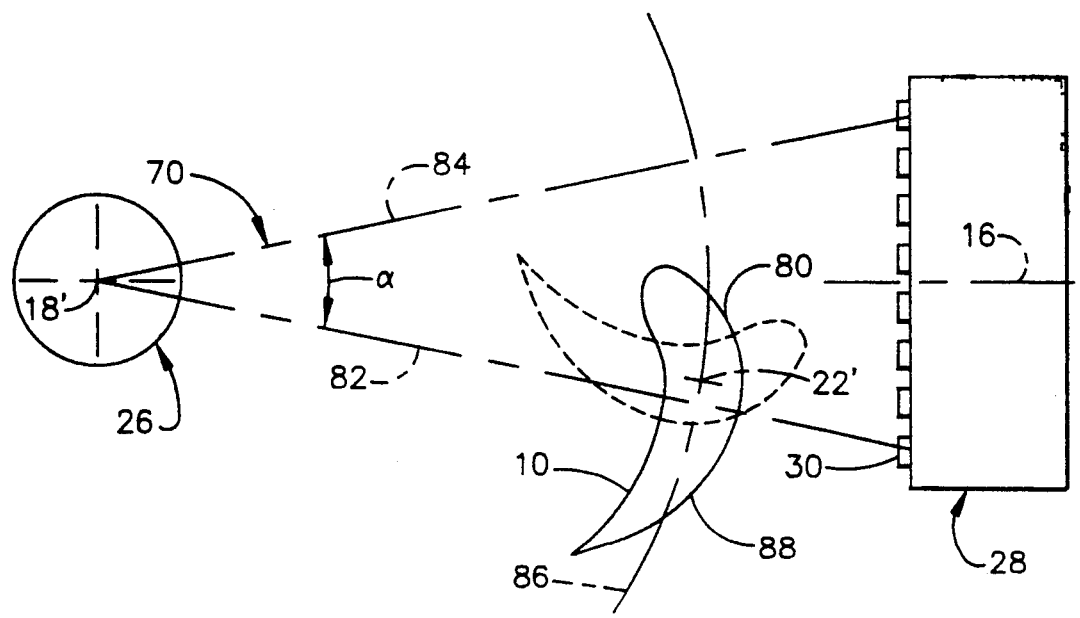
FIGS. 3A and 3B are detailed top elevation views showing the steps employed in the CT x-ray inspection system in accordance with the present invention.
Figure 3B:
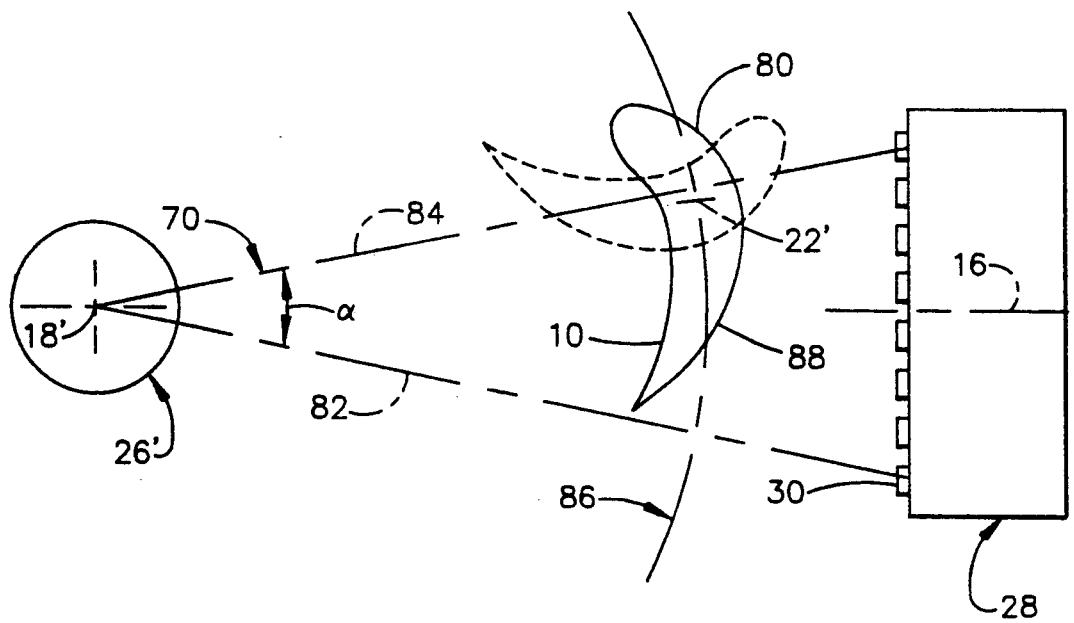

FIG. 2 illustrates an industrial computed tomography system 24 in accordance with the present invention. System 24 includes an x-ray source 26, such as a Philips MG model 450 420 kV high stability constant potential x-ray system, a Lintron 2 MeV source or the like, and an x-ray detector 28 such as a Xenon gas-type detector, solid state scintillator or the like. If a Xenon-type detector, detector 28 may be a 12-inch active length Xenon linear array detector, as manufactured by the General Electric Company, having about 1,280 elements 30, as best shown in FIGS. 3A and 3B, which collectively provide an inherent resolution of about 20 mils. Higher resolutions are possible by using known multiple sampling schemes. Detector elements 30 are preferably spaced in the linear array on centers of about 0.005 inches to about 0.01 inches to provide the high resolution.

X-ray source 26 and detector 28 are mounted to a gantry-type structure 32 by saddle members 34 and 36, respectively. Gantry structure 32 includes at least one vertical member 38 and a horizontal member 40 extending from vertical member 38. A second vertical member 42, partially shown in FIG. 2, may be provided for additional support.

Saddle member 34 and detector 26 may be moved linearly along horizontal member 40 by a servomotor 44 in the directions indicated by axis U. The spacing between source 26 and detector 28 may be adjusted according to the size of the component under test to prevent contact between the component and the CT system during examination. Detector 28 and its associated saddle member 36 may be stationary or saddle 36 may be interconnected to source saddle 34 to permit coordinated motion of both source 26 and detector 28. Horizontal member 40 may also be moved along axis Z by servomotor 46 to control the elevation of source 26 and detector 28.

A part manipulator 48 is located at the base of gantry structure 32 for controlling the motion of a component part under inspection relative to source 26 and detector 28. Part manipulator 48 preferably includes two linear axes of motion, indicated by directional arrows X and Y, and three rotary axes of motion indicated by arrows A, B and C. Motion along linear axes X and Y is controlled by known techniques such as servomotors and gear combinations 50 and 52. Rotary platforms 54, 56 and 58 respectively permit rotary motion about rotary axes A, B and C respectively. Each platform 54, 56 and 58 includes a servomotor 60 (only one shown in FIG. 2 for clarity) to control rotary motion of the respective platforms. Platform 54 includes a fixture 62 for mounting a component part to be examined.

CT system 24 is housed in a system enclosure 64 which is designed in accordance with Bureau of Radiological Health (BRH) requirements for x-ray systems and further shall meet all government radiation standards for installations of this type.

Figure 3C:
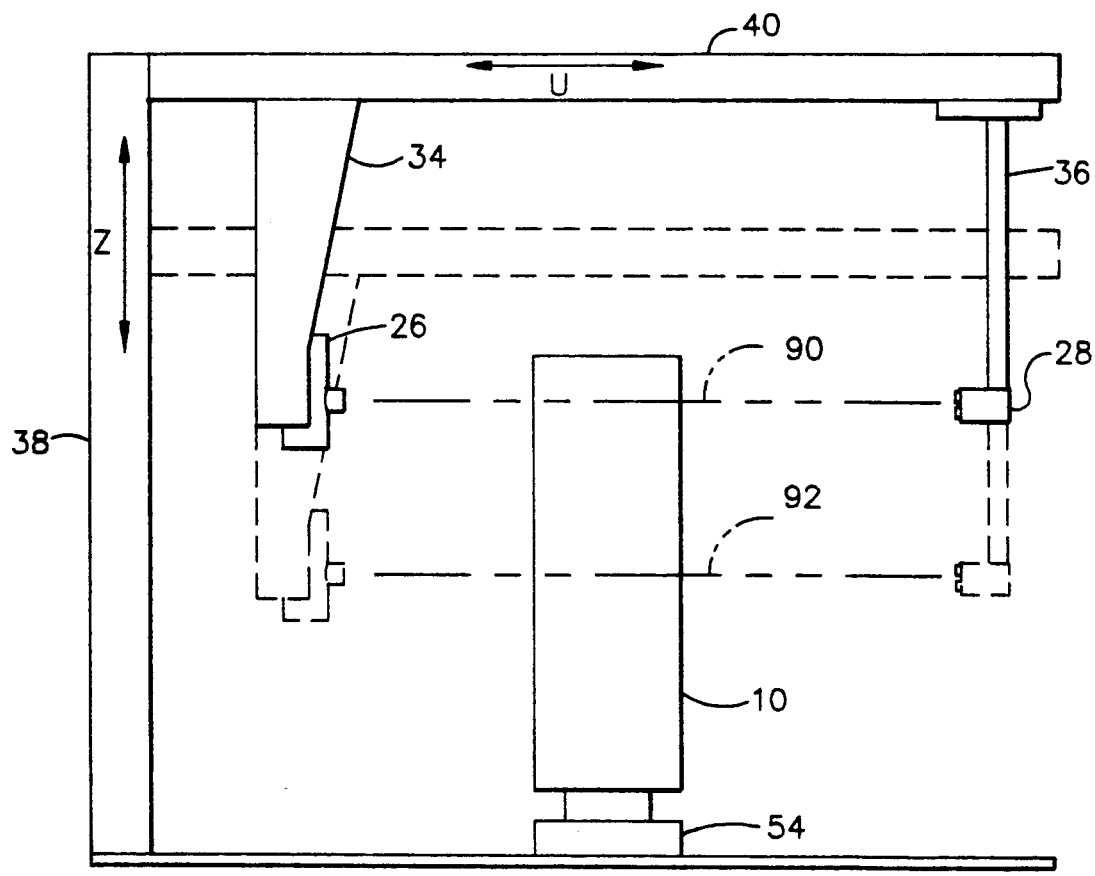
FIG. 3C is a detailed side elevation view showing a step employed in the CT x-ray inspection system in accordance with the present invention.

A system computer 66 is provided to control operation of CT system 24. A data acquisition system (DAS) 68 receives electrical signals from detector 28 which correspond to the attenuated x-ray beam 70 that passes through a part under inspection; DAS 68 converts the low voltage analog detector change signals received to a quantified digital value which is stored and later recalled for multiplexing with other received and converted signals to reconstruct a cross-sectional image of a component 10 being examined (FIGS. 3A-3C).

An operator console 72 is provided to permit control of the CT scanning system 24 and also provides an operator interface with a manipulator control 74 which controls operation of part manipulator 48. Operator console 72 includes a plurality of CRT's 73 to permit display of cross-sectional images of component 10. CRT's 73 may also be interconnected to one or more video cameras 76 which permit observation of CT system 24 during operation.

Communications between CT scan system 24 and the combination of computer 66, DAS 68 and operator console 72 is accomplished through a plurality of communications links indicated by broken line 78. Electrical signals may be sent by an operator through one of communications links 78 to control operation of part manipulator 48 and to control operation of x-ray source 26 and detector 28. The electrical signals, corresponding to the attenuated x-ray beam that passes through component 10, are also transmitted from detector 28 to computer 66 and DAS 68 by one of communications links 78.

Referring to FIGS. 3A and 3B, in accordance with the present invention, the component 10 to be inspected is mounted in fixture 62 (FIG. 2) and moved by manipulator 48 within the fan angle of fan beam 70. Component 10 is moved within the x-ray fan beam 70 so that a first portion 80 of component 10 to be scanned is within the boundaries 82 and 84 of the fan beam and does not extend beyond boundary 84. X-ray beam 70 may have a fan beam angle alpha between about 5° and about 30°. After beam 70 is generated by x-ray source 26, component 10 is rotated 360° around component inspection rotational axis 22'. The attenuated x-ray beam that passes through component part 10 during rotation is collected by elements 30 of detector 28. Detector 28 generates a multiplicity of electrical signals responsive to the collected attenuated x-ray beam which are transmitted to computer 66 and DAS 68 by communications links 78.

In accordance with the present invention, component 10 is incrementally moved or rotated along an arc 86 to bring a next portion 88 of component 10, adjacent to and integral with portion 80, within beam 70 for inspection (FIG. 3B). Component 10 is moved along arc 86 by the X and Y axes of manipulator 48 so that component inspection rotational axis 22' remains at a constant, selected radius from x-ray source focal point 18'. After positioning component 10 so that next portion 88 of the component 10 will be within the x-ray beam, an operator can activate x-ray source 26 to generate beam 70 and the rotation of component 10 360° around component inspection rotational axis 22' is repeated. Again, the attenuated x-ray beam that passes through component 10 during rotation is collected by elements 30 of detector 28 and converted to a multiplicity of electrical signals responsive to the collected attenuated x-ray beam. These electrical signals are further transmitted to computer 66 and data acquisition system 68 by communications links 78.

If the component under test is larger than component 10, as illustrated in FIGS. 3A and 3B, then additional incremental rotations along arc 86 and 360° rotations around axis 22' may be required to reconstruct a complete image of the component. Once all portions of component 10 have passed through beam 70 and been rotated around component inspection rotational axis 22', the digitized electrical signals stored during each iteration of this rotate/rotate operation may be combined to reconstruct a cross-sectional image of the component at a selected plane 90 or slice through the component as shown in FIG. 3C. The image may be displayed on one of the CRT's 73 mounted in operator console 72 for analysis.

Thus, the rotate/rotate method of the present invention requires only one complete pass of component 10 through x-ray beam 70 to acquire sufficient data to reconstruct a cross-sectional image through the component 10 at the selected elevation corresponding to plane 90; this one complete pass is divided into incremental rotational steps about the source focal point 18', as described hereinabove, to expose each portion of the component 10 to the x-ray beam 70 and at each incremental rotational step, the component 10 is rotated 360° about its inspection rotational axis 22'.

After reconstructing an image of one slice through component 10, another slice or image through component 10 may be taken at a different elevation by moving gantry horizontal member 40 along the Z axis as shown in FIG. 3C. Source 26 and detector 28 are therefore moved parallel to the inspection rotational axis to construct another cross-sectional image of the component at a different selected plane 92 through component 10 perpendicular to the inspection rotational axis 22'. Again, a first portion 80 of component 10 would be moved within x-ray beam 70 and then rotated 360° around rotational axis 22'. Component 10 would then be incrementally rotated around x-ray focal point 18' until the next portion of component 10 is within the field of view of beam 70. This rotate/rotate operation would be repeated until all portions of component 10 have passed through the field of view of beam 70 and each portion has been rotated 360° around rotational inspection axis 22' to provide a complete cross-sectional image of component 10 at the different selected elevation through component 10 corresponding to plane 92.

The images at different elevations through component 10 may be displayed on CRT's 73 for analysis or hard copies of the different images may be printed by the operator console 72 or a remote printer (not shown in FIG. 2).

While FIG. 2 shows the elevation of the CT system being changed by moving gantry horizontal member 40 along the Z-axis, those skilled in the art will recognize that means could equally be provided to change the elevation of part manipulator 48.

Figure 1:
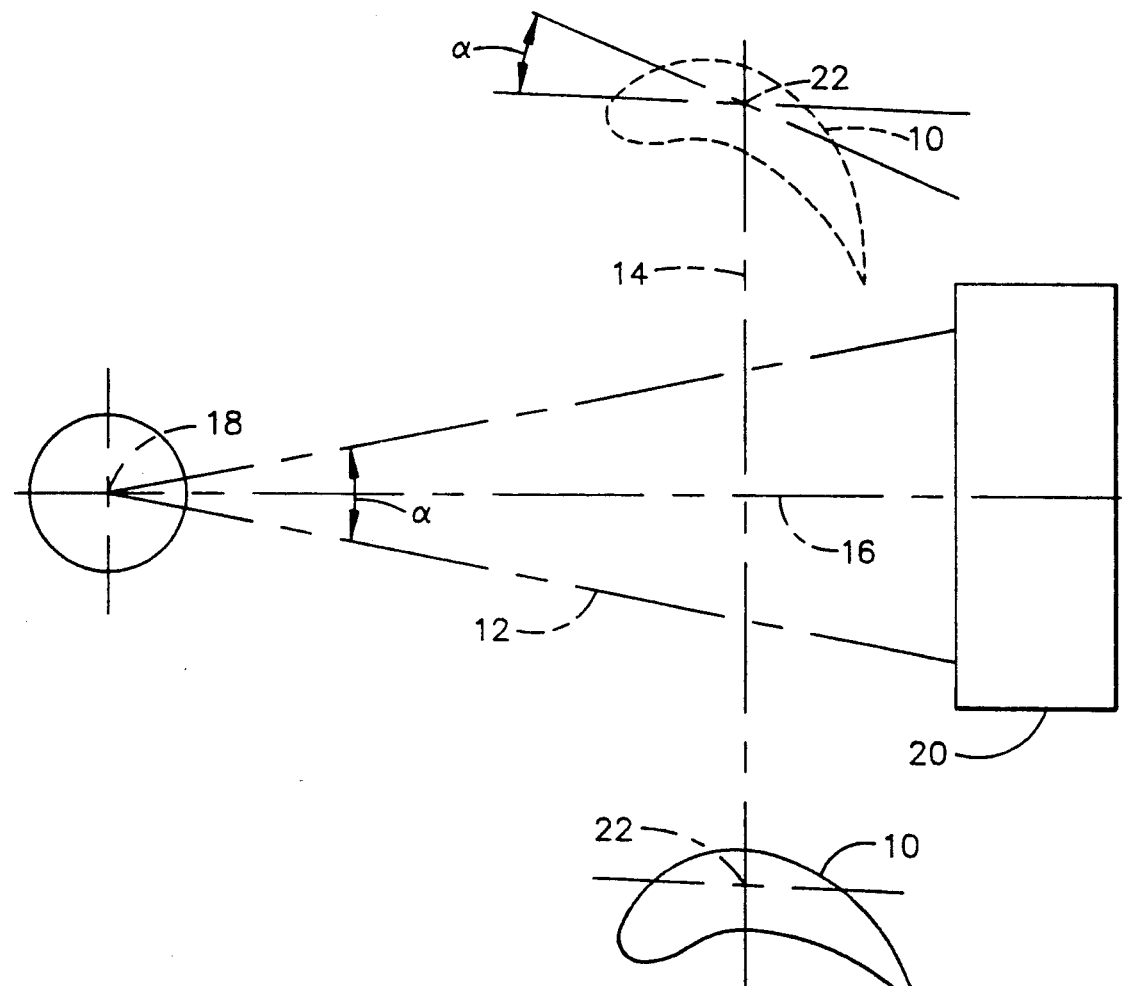
FIG. 1 is a top elevation view showing the steps employed in a rotate/translate CT x-ray inspection system.

The rotate/rotate CT operation, as previously described, requires only one pass of the component through beam 70, as opposed to multiple passes required with a rotate/translate method described with respect to FIG. 1. Additionally, less computer capacity and computation time is required with the rotate/rotate method because the geometry of component 10 remains constant relative to x-ray source focal point 18' by moving component inspection rotational axis 22' along arc 86 at a constant radius from focal point 18'. Thus, the present invention permits rapid and efficient inspection of gas turbine engine components, rocket engine components or the like, and is easily adapted to an automated inspection environment.

It will be readily understood by those skilled in the art that the present invention is not limited to the specific embodiment described and illustrated herein. Different embodiments and illustrations besides those shown herein and described, as well as the variations, modifications and equivalent arrangements will now be apparent or will be reasonably suggested by the foregoing specification and drawings without departing from the substance or scope of the invention. While the present invention has been described herein in detail in relation to its preferred embodiments, it is to be understood that this disclosure is only illustrative and exemplary of the present invention and is made merely for purposes of providing a full and enabling disclosure of the invention. Accordingly, it is intended that the invention be limited only by the spirit and scope of the claims appended hereto.

What is claimed is:

1. A method for inspecting a component having a dimension larger than a fan beam of an x-ray inspection system, comprising the steps of:
    (a) providing an x-ray beam having a selected fan angle and a source focal point;
    (b) positioning a first portion of the component substantially completely within the x-ray beam;
    (c) rotating the component 360 degrees around a component inspection rotational axis;
    (d) collecting an attenuated x-ray beam that passes through the component during rotation;

(e) generating a multiplicity of electrical signals responsive to the collected attenuated x-ray beam;

(f) incrementally moving the component inspection rotational axis around the x-ray source focal point to position a next portion of the component within the x-ray beam, the component inspection rotational axis being maintained at a selected radius from the x-ray source focal point;

(g) repeating steps (c), (d), (e) and (f) until all portions of the component to be inspected have passed through the x-ray fan beam; and (h) combining the electrical signals from step (e) to construct a cross-sectional image of the component at a selected plane through the component.

2. The method of claim 1, further comprising the step of moving the x-ray beam focal point and an x-ray beam detector parallel to the inspection rotational axis to construct another cross-sectional image of the component at a different selected plane through the component perpendicular to the inspection rotational axis.

3. The method of claim 1, wherein the selected x-ray fan angle is between about 5° and about 30°.

4. The method of claim 1, wherein step (f) comprises the step of rotating the component inspection rotational axis around the x-ray source focal point by an angle equal to about the selected fan angle to ensure that all portions of the component to be inspected fall within the x-ray beam during at least one 360° rotation around the component inspection rotational axis.

5. The method of claim 1, wherein the attenuated x-ray beam is collected by a xenon gas detector having a multiplicity of detector elements formed in a linear array.

6. The method of claim 5, wherein the detector elements are mounted in the detector at a spacing between about 0.005 inches and about 0.01 inches.

7. The method of claim 1, wherein the attenuated x-ray beam is collected by a solid state scintillator.

8. The method of claim 1, further comprising the step of moving the component along the component inspection rotational axis to construct another cross-sectional image of the component at a different selected plane through the component perpendicular to the inspection rotational axis.

9. The method of claim 1, further comprising the step of storing the electrical signals for each portion of the component inspected to facilitate reconstruction of a cross-sectional image of substantially the entire component.

10. The method of claim 1, further comprising the step of choosing the selected radius to prevent the part from contacting the x-ray inspection system during step (c).

11. The method of claim 1, wherein the part inspection rotational axis is located proximate to a geometric center of the component cross-section to be reconstructed.

12. A CT x-ray system for inspecting a component having a dimension larger than a fan beam of the system, comprising:

an x-ray source for generating a beam having a focal point;

first means for rotating the component 360° around a component inspection rotation axis with at least a portion of the component within the x-ray beam;

component manipulator means having at least two linear axes of motion for incrementally rotating the component around the x-ray source focal point to position another portion of the component within the x-ray beam, said component inspection rotational axis being maintained at a selected radius from the x-ray source focal point; and detector means for collecting an attenuated x-ray beam which passes through the component to reconstruct a component cross-sectional image at a selected plane through the component.

13. The CT system of claim 12, further comprising a gantry structure having at least one vertical member and a horizontal member extending outwardly from said at least one vertical member, said x-ray source and said detector means both being mounted to said horizontal member at a spacing from each other and said horizontal member being movably mounted to said vertical member to permit vertical movement of said x-ray source and said detector relative to the component under inspection such that a cross-sectional image may be reconstructed at a multiplicity of different selected planes through the component.

14. The CT system of claim 12, wherein the detector means is a xenon gas detector having a multiplicity of detector elements formed in a linear array.

15. The CT system of claim 14, wherein the detector elements are mounted in the detector at a spacing between about 0.005 inches and 0.01 inches.

16. The CT system of claim 14, wherein the xenon gas detector comprises a sufficient number of detector elements to provide an inherent resolution of at least about 20 mils.

17. The CT system of claim 16, wherein the xenon gas detector comprises about 1,280 detector elements.

* * * * *